United States Patent [19]
Baldus et al.

[11] Patent Number: 5,316,766
[45] Date of Patent: May 31, 1994

[54] THROMBOSIS TREATMENT WITH FIBRINOLYTICS AND PROSTACYCLINS

[75] Inventors: Berthold Baldus; Bernhard Maass; Bernd Müller; Werner Witt, all of Berlin, Fed. Rep. of Germany

[73] Assignee: Schering Aktiengesellschaft, Berlin and Bergkamen, Fed. Rep. of Germany

[21] Appl. No.: 474,689

[22] Filed: Feb. 6, 1990

Related U.S. Application Data

[63] Continuation of Ser. No. 316,841, Feb. 28, 1989, abandoned, which is a continuation of Ser. No. 941,444, Dec. 15, 1986, abandoned.

[30] Foreign Application Priority Data

Dec. 13, 1985 [DE] Fed. Rep. of Germany ....... 3544663

[51] Int. Cl.$^5$ .................. A61K 37/54; A61K 37/547; A61K 31/215
[52] U.S. Cl. .............. 424/94.63; 424/94.64; 514/530; 514/822; 514/824
[58] Field of Search ............ 424/94.63, 94.64; 514/530, 822, 824

[56] References Cited

U.S. PATENT DOCUMENTS 4,496,745  1/1985  Amemiya et al. ................. 549/215
4,839,169  6/1989  Whittle .............................. 424/94.3

FOREIGN PATENT DOCUMENTS 0257859  8/1987  European Pat. Off. ...... A61K 37/54

OTHER PUBLICATIONS

Chem. Abst., 103:98516r, 1985.
Schumacher et al., "Augmentation of Streptokinase-Induced Thrombolysis by Heparin and Prostacyclin", Journal of Cardiovascular Pharmacology, 7:739-746, 1985.
FASEB 68th Annual Meeting APS, ASPET, AAP, AIN, St. Louis, Mo., Apr. 1-6, 1984, Proceedings, Coronary Pharmacology Abstracts, p. 335, No. 297, Schumacher et al., "Streptokinase (SK) Thrombolysis in Dogs: Potentiation by Heparin (H) and Prostacyclin (PGI$_2$)".
Blasko et al., Drugs Exptl. Clin. Res., IX, (7), 505-506 (1983).
Szczeklik et al., Thrombosis Research, 29, 655-660 (1983).

*Primary Examiner*—John W. Rollins
*Attorney, Agent, or Firm*—Millen, White, Zelano & Branigan

[57] ABSTRACT

The combination of a fibrinolytic and a prostacyclin analogue is very useful for thrombosis treatment, especially to avoid subsequent rethrombosis.

24 Claims, No Drawings

THROMBOSIS TREATMENT WITH FIBRINOLYTICS AND PROSTACYCLINS

This application is a continuation of application Ser. No. 07/316,841, filed Feb. 28, 1989, now abandoned, which is a continuation of Ser. No. 06/94/444, filed Dec. 15, 1986 now abandoned.

BACKGROUND OF THE INVENTION

This invention relates to the use of a combination of a fibrinolytic and a prostacyclin analogue for thrombosis treatment, and to the corresponding combination product.

According to K. H. Gold et al. Circulation 68, I-50 to I-54 (1983) and W. Ganz et al. Amer. Heart J. 101, 4 (1981), the recurrence of thrombosis (rethrombosis) after an initially successful thrombolysis, continues to represent a problem in fibrinolytic therapy. As pathogenic mechanisms, these mention the presence of a damaged and thus a thrombogenic vascular inner wall on the originally thrombosed site after dissolution of thrombi, and in many cases a bleeding anomaly induced by stenoses. Thrombogenic surfaces and rheological disturbances result in renewed activation of the plasma clotting system and thrombocytes (platelets).

In his article "Pharmacology of Streptokinase" (from the manual "Experimental Pharmacology 46: Fibrinolytics and Antifibrinolytics, F. Markward (ed.), Springer-Verlag, Berlin-Heidelberg-New York, 1978, 151–177), H. P. Kloecking writes that, particularly after thrombolysis with streptokinase and urokinase but to a lesser extent also after use of t-PA and pro-urokinase, cleavage products of fibrinogen and fibrin occur. These result in an increased aggregation tendency of platelets and thus promote quick new growth of platelet thrombi on the original site of a lysed thrombus.

Current clinical prophylaxis of fast rethromboses involve the inhibition of plasmatic clotting by heparin. E. Hiller comments on this in the Muenchner medizin. Wochenschrift 126, 13 (1984). He considers a prophylaxis with heparin as problematic, since platelet-induced rethromboses are not thereby prevented. According to his data, these are more likely even promoted. According to Kloecking, because of the consumption of the clotting factors, the plasmatic clotting system is no longer fully functioning especially after thrombolysis with streptokinase or urokinase. By the additional administration of heparin, thus, the danger of bleeding is promoted.

To what extent platelets and to what extent the plasmatic clotting system are involved in rethrombosis is indeed often discussed but still has not been clarified.

SUMMARY OF THE INVENTION

It is an object of this invention to provide a new product and method of thrombolysis which also prevents and/or lowers or minimizes the probability of a rethrombosis after thrombolysis.

Upon further study of the specification and appended claims, further objects and advantages of this invention will become apparent to those skilled in the art.

These objects have been achieved based on the findings that rethrombosis after thrombolysis can be prevented and/or made less likely by administration of fibrinolytics and prostacyclin analogues together for dissolution of thrombi.

Activation, aggregation and adhesion of platelets have a decisive role in rethrombosis after successful thrombolysis. By the action of the prostacyclin analogues in inhibiting platelet aggregation, no rethrombosis occurs from the beginning of the treatment.

Suitable prostacyclin analogues for use according to this invention include carbacyclin derivatives, e.g., those described in U.S. Pat. No. 4,692,464 which is a divisional application of U.S. Ser. No. 086,506, filed Oct. 19, 1979 (equivalent to DE-OS-2845770) now abandonded; U.S. Ser. No. 745,989, filed Jun. 18, 1985, now abandonded which is a continuation of U.S. Ser. No. 464,550, filed Feb. 7, 1983 now abandonded (equivalent to DE-OS-3204443); U.S. Ser. No. 803,453 of Nov. 29, 1985, now abandonded which is a continuation of Ser. No. 581,851 of Feb. 2, 1984 (equivalent to DE-OS-3306123); U.S. Ser. No. 859,977 of May 5, 1986, now abandonded which is a continuation of Ser. No. 510,121 of Jul. 1, 1983 (equivalent to DE-OS 3226550) now abandonded; inter alia, all of which documents are entirely incorporated by reference herein.

Other suitable prostacyclin analogues are the prostacyclins per se, e.g., as disclosed in U.S. Pat. Nos. 4,191,694; 4,219,479; 4,315,013; 4,364,950; 4,378,370; 4,466,969 in each case, suitable species being routinely selected in accordance with whether they have thrombocyte aggregation inhibition activity.

More generally, this invention relates to the combination of a fibrinolytic with any agent having thrombocyte aggregation inhibition activity, the use of such a combination being analogous to that described herein for the combination of a fibrinolytic with a prostacyclin analogue.

Preferred carbacyclins for use according to the invention are:

5-{(E)-(1S,5S,6R,7R)-7-hydroxy-6-[(E)-(3R,4RS)-3-hydroxy-4-methyl-oct-1-en-6-yl]-bicyclo[3.3.0]octan-3-ylidene}-pentanoic acid (Iloprost)

(5E)-(16RS)-13,14-didehydro-16,20-dimethyl-18,18,19,19-tetradehydro-6a-carbaprostaglandin-$I_2$, (5E)-(16RS)-13,14-didehydro,1a, 1b-dihomo-16,20-dimethyl-3-oxa-18,18,19,19,-tetradehydro-6a-carba-prostaglandin-$I_2$ or 5-(E)-{1S,5S,6S,7R)-7-hydroxy-6-[(3S,4S)-3-hydroxy-4-methyl-nona-1,6-diinyl]-bicyclo[[3.3.0]octan-3-ylidene}-3-oxa-pentanoic acid.

Streptkokinase, urokinase and t-PA, as well as pro-urokinase and pro t-PA, are suitable as fibrinolytics.

The carbacyclins are administered in amounts in the range otherwise customary for inhibition of platelet aggregation. The precise amount to be used per this invention depends on the extent of the thrombosis and the rethrombosis which is expected, as well as on the usual factors affecting precise dosage determination for a given patient. The amount of fibrinolytic used is the same as or less than would otherwise be used according to conventional therapy with the particular fibrinolytic involved. Thus, the administration of each agent of the combination per this invention is analogous to the conventional administration of the respective individual agents for purposes of thrombolysis (the fibrinolytic) or platelet aggregation inhibition (the prostacyclin analogue).

A typical human unit dose of the prostacyclin analogue for use in this invention is, depending on the mode of application, 10 pg to 1 mg i.v. or 10 μg to 500 mg p.o., preferably 0.1 to 100 μg, most preferably 0.091–10 μg/kg body mass/min. of Iloprost i.v. or a biologically equivalent amount of another prostacyclin analogue. A typical unit dose of the fibrinolytic agent is 5000 IU to ten million IU of streptokinase, preferably 50,000–5,000,000 IU, most preferably 250,000–2,000,000 IU or a biologically equivalent amount of another fibrinolytic agent. Typically, the weight ratio of fibrinolytic to prostacyclin analogue is about $10^7:1$ to about $10^2:1$, preferably $10^5:1$ to about $10^3:1$.

The total dose of the combination of this invention is normally achieved by administration of a correspondingly lower dosage, e.g., parenterally, over a period of time, e.g., 1–6 hrs.

Normally, both agents are administered simultaneously for the same period of time. However, it is also possible to commence the administration of the prostacyclin analogue prior to or after initiation of the fibrinolytic agent. It is also possible to continue the treatment of the prostacyclin analogue after the termination of the fibrinolytic agent.

The two kinds of agents can be administered in the same dosage unit or can be administered in separate dose units. They can be administered to mammals, including humans, in the forms of conventional galenic formulations, for example, as described in the preceding references.

The combination according to the invention is preferably infused or injected intrasmuscularly. In the case of parenteral use of streptokinase, urokinase, t-PA, prourokinase and pro-tPA, the carbacyclins used in the combination can also be administered orally.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following example, all temperatures are set forth uncorrected in degrees Celsius and all parts and percentages are by weight; unless otherwise indicated.

EXAMPLE

Catheters for infusion and electric stimulation by peripheral arteries were placed in the left descending coronary artery on 10 anesthetized beagle dogs (anesthesia with Tramadol, 2 mg/kg i.v.+0.5 mg/kg/h i.v.; Imbretil ®, 0.33 mg/kg i.v., $N_2O/O_2$ 80:20). Intracoronary stimulation with a current intensity of 250 uA was continuously applied for thrombus induction. The growth of a coronary thrombus up to complete occlusion was assessed in 15-minute intervals by intracoronary injection of the contrast medium Urografin ® 76 with X-ray control. With complete occlusion of the coronary artery, streptokinase (250 I.U./kg/min) was infused intracoronarily until recirculation was determined by X-ray. In 5 animals only streptokinase was infused intravenously, in the other 5 animals, the prostacyclin analogue Iloprost (50 ng/kg/min) was additionally infused intravenously.

Results

In 10/10 animals, the streptokinase infusion, in an average of 60 min., resulted in the reopening of the coronary artery previously completely occluded by thrombosis.

In 5/5 dogs which received streptokinase solely, on an average of 21 min. after reopening, a complete reocclusion by rethrombosis occurred spontaneously.

When, in addition to streptokinase, Iloprost was infused intravenously, rethrombosis did not occur in any of the 5 animals within this period. Also, no rethrombosis occurred on one dog which, in addition to streptokinase, received, instead of Iloprost, 5-{(E)-(1S,5S,6S,7R)-7-hydroxy-6-[(3S,4S)-3-hydroxy-4-methyl-nona-1,6-diinyl]bicyclo-[3.3.0]octan-3-ylidene}-3-oxapentanoic acid in a dosage of 5 ng/kg/min.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition useful for thrombosis treatment comprising an effective amount of a fibrinolytic agent and an amount of a carbacyclin effective to inhibit thrombocyte aggregation.

2. A composition of claim 1, wherein the fibrinolytic agent is streptokinase.

3. A composition of claim 2, wherein the carbacyclin is Iloprost.

4. A composition of claim 2, wherein the carbacyclin is 5-{(E)-(1S,5S,6S,7R)-7-hydroxy-6-[(3S,4S)-3-hydroxy-4-methyl-nona-1,6-diinyl]-bicyclo[3.3.0]octan-3-ylidene}-3-oxapentanoic acid.

5. A pharmaceutical composition useful for thrombosis treatment comprising an effective amount of a fibrinolytic agent which is t-PA and an amount of a carbacyclin effective to inhibit thrombocyte aggregation.

6. A composition of claim 1, wherein the fibrinolytic agent is urokinase, pro-urokinase or pro t-PA.

7. A composition of claim 1, wherein the carbacyclin is Iloprost.

8. A composition of claim 1, wherein the carbacyclin is
(5E)-(16RS)-13,14-didehydro-16,20-dimethyl-18,18,19,19-tetradehydro-6a-carbaprostaglandin-$I_2$,
(5E)-(16RS)-13,14-didehydro,1a,1b-dihomo-16,20-dimethyl-3-oxa-18,18,19,19-tetradehydro-6a-carbaprostaglandin-$I_2$ or 5-(E)-{1S,5S,6S,7R)-7-hydroxy-6-[(3S,4S)-3-hydroxy-4-methylnona-1,6-diinyl]-bicyclo[[3.3.0]octan-3-ylidene}-3-oxapentanoic acid.

9. A composition of claim 1, wherein the carbacyclin is 5-{(E)-(1S,5S,6S,7R)-7-hydroxy-6-[(3S,4S)-3-hydroxy-4-methyl-nona-1,6-diinyl]-bicyclo[3.3.0]octan-3-ylidene}-3-oxapentanoic acid.

10. A composition of claim 1, wherein the weight ratio of fibrinolytic agent to carbacyclin is $10^7:1$ to $10^2:1$.

11. A composition of claim 1, wherein the amount of carbacyclin is 10 ng to 1 mg of Iloprost or a biologically equivalent amount of another carbacyclin.

12. A composition of claim 1, wherein the amount of fibrinolytic agent is 5000 IU to 1 million IU of streptokinase or a biologically equivalent amount of another fibrinolytic agent.

13. A method of treating thrombosis while reducing or preventing the risk of rethrombosis in a patient in need of such treatment, comprising administering an effective amount of the composition of claim 1 to the patient, whereby the extent of rethrombosis occurring after said administration is reduced in comparison to that occurring after administration of the fibrinolytic alone.

14. A method of treating thrombosis while reducing or preventing the risk of rethrombosis in a patient in need of such treatment, comprising administering an effective amount of the composition of claim 2 to the patient, whereby the extent of rethrombosis occurring after said administration is reduced in comparison to that occurring after administration of the fibrinolytic alone.

15. A combination of claim 5, wherein the carbacyclin is iloprost.

16. A method of treating thrombosis while reducing or preventing the risk of rethrombosis in a patient in need of such treatment, comprising administering an effective amount of the composition of claim 5 to the patient, whereby the extent of rethrombosis occurring after said administration is reduced in comparison to that occurring after administration of the fibrinolytic alone.

17. A method of treating thrombosis while reducing or preventing the risk of rethrombosis in a patient in need of such treatment, comprising administering an effective amount of the composition of claim 7 to the patient, whereby the extent of rethrombosis occurring after said administration is reduced in comparison to that occurring after administration of the fibrinolytic alone.

18. A method of treating thrombosis while reducing or preventing the risk of rethrombosis in a patient in need of such treatment, comprising administering an effective amount of the composition of claim 8 to the patient, whereby the extent of rethrombosis occurring after said administration is reduced in comparison to that occurring after administration of the fibrinolytic alone.

19. A method of treating thrombosis while reducing or preventing the risk of rethrombosis in a patient in need of such treatment, comprising administering an effective amount of the composition of claim 3 to the patient, whereby the extent of rethrombosis occurring after said administration is reduced in comparison to that occurring after administration of the fibrinolytic alone.

20. A method of treating thrombosis while reducing or preventing the risk of rethrombosis in a patient in need of such treatment, comprising administering an effective amount of a carbacyclin and an effective amount of a fibrinolytic agent, whereby the extent of rethrombosis occurring after said administration is reduced in comparison to that occurring after administration of the fibrinolytic alone.

21. A method of claim 20, wherein the administration of the tPA and the carbacyclin is simultaneously.

22. A method of claim 20, wherein the administration of the tPA and the carbacyclin is sequential.

23. A method of reducing or preventing the risk of rethrombosis in a patient receiving or having received treatment for thrombosis comprising administering to said patient an amount of a carbacyclin effective to inhibit the aggregation of thrombocytes.

24. A kit comprising an effective amount of a fibrinolytic agent and an amount of a carbacyclin effective to inhibit thrombocyte aggregation, wherein the fibrinolytic agent and the carbacyclin are present in separate dosage units.

* * * * *